US006641817B1

(12) United States Patent
Coffin et al.

(10) Patent No.: US 6,641,817 B1
(45) Date of Patent: Nov. 4, 2003

(54) HERPES VIRUS VECTORS FOR DENDRITIC CELLS

(75) Inventors: Robert Stuart Coffin, London (GB); Benjamin Chain, London (GB)

(73) Assignee: Biovex Limited, London (GB)

( * ) Notice: Subject to any disclaimer, the term of this patent is extended or adjusted under 35 U.S.C. 154(b) by 0 days.

(21) Appl. No.: 09/744,942

(22) PCT Filed: Aug. 2, 1999

(86) PCT No.: PCT/GB99/02529

§ 371 (c)(1),
(2), (4) Date: Aug. 6, 2001

(87) PCT Pub. No.: WO00/08191

PCT Pub. Date: Feb. 17, 2000

(30) Foreign Application Priority Data

Jul. 31, 1998 (GB) ............................................... 9816781

(51) Int. Cl.$^7$ ...................... A61K 39/245; A61K 48/00; C12N 7/00; C12N 7/01; C12N 15/869
(52) U.S. Cl. ................................ 424/199.1; 424/205.1; 424/231.1; 424/93.2; 424/93.21; 435/235.1; 435/236; 435/320.1; 435/325; 435/372
(58) Field of Search ............................ 435/235.1, 236, 435/320.1, 325, 372; 424/199.1, 205.1, 229.1–231.1, 93.2, 93.21

(56) References Cited

FOREIGN PATENT DOCUMENTS

| WO | 94/03207 | * | 2/1994 | .......... | A61K/39/12 |
|----|----------|---|--------|-----------|------------|
| WO | WO 98/04726 |  | 2/1998 |  |  |
| WO | WO 98/51809 |  | 11/1998 |  |  |

OTHER PUBLICATIONS

Fields Virology, Third edition. Ed. B.N. Fields et al. vol. 2, pp. 2234 & 2454. Lippincott Williams & Wilkins, Philadelphia. 1996.*
Coffin et al, "Pure populations of transduced primary human cells can be produced using GBP expressing herpes virus vectors and flow cytometry", Gene Therapy, vol. 5, May 1998, pp. 718–722.
Coffin et al, "Gene delivery to the central and peripheral nervous systems of mice using HSV1 ICP34.5 deletion mutant vectors", Gene Therapy, vol. 3, No. 10, Oct. 1996, pp. 886–891.
MacLean et al, "Herpes simplex virus type 1 deletion variants 1714 and 1716 pinpoint neurovirulence–related sequences in Glasgow strain 17+ between immediae early gene 1 and the 'a' sequence", Journal of General Virology 72:631–639 (1991).
Chou et al, "Differential Response of Human Cells to Deletions and Stop Codons in the $_{\gamma_1}$34.5 Gene of Herpes Simplex Virus", Journal of Virology 68(12):8304—8311 (1994).

Chou and Roizman, The $_{\gamma_1}$34.5 gene of herpes simplex virus 1 precludes neuroblastoma cells from triggering total shutoff of protein synthesis characteristic of programed cell death in neuronal cells, Proc. Natl. Acad. Sci. USA 89:3266–3270 (1992).
Gendler et al, "Molecular Cloning and Expression of Human Tumor–associated Polymorphic Epithelial Mucin", The Journal of Biological Chemistry 265(25):15286–15293 (1990).
Aicher et al, "Successful retroviral mediated transduction of a reporter gene in human dendritic cells: Feasibility of therapy with gene–modified antigen presenting cells", Experimental Hematology 25:39–44 (1997).
Samaniego et al, "Functional Interactions between Herpes Simplex Virus Immediate–Early Proteins during Infection: Gene Expression as a Consequence of ICP27 and Different Domains of ICP4", Journal of Virology 69(9):5705–5715 (1995).
Zitvogel et al, "Therapy of Murine Tumors with Tumor Peptide–pulsed Dendritic Cells: Dependence on T Cells, B7 Costimulation, and T Helper CII 1–associated Cytokines", J. Exp. Med. 183:87–97 (1996).
Celluzzi et al, "Peptide–pulsed Dendritic Cells Induce Antigen–specific, CTL–mediated Protective Tumor Immunity", J. Exp. Med. 183:283–297 (1996).
Reeves et al, "Retroviral Transduction of Human Dendritic Cells with a Tumor–associated Antigen Gene", Cancer Research 56:5672–5677 (1996).
Arthur et al, "A comparison of gene transfer methods in human dendritic cells", Cancer Gene Therapy 4(1):17–25 (1997).
Ace et al, "Construction and Characterization of a Herpes Simplex Virus Type 1 Mutant Unable To Transinduce Immediate–Early Gene Expression", Journal of Virology 63(5):2260–2269 (1989).
Smith et al, "Evidence That The Herpes Simplex Virus Immediate Early Protein ICP27 Acts Post–Transcriptionally during Infection to Regulate Gene Expression", Virology 186:74–66 (1992).
Rice and Knipe, "Genetic Evidence for Two Distinc Transactivation Functions of the Herpes Simplex Virus α Protein ICP27", Journal of Virology 64():1704–1715 (1990).

(List continued on next page.)

Primary Examiner—Mary E. Mosher
(74) Attorney, Agent, or Firm—Nixon & Vanderhye, P.C.

(57) ABSTRACT

An attenuated herpes virus capable of efficiently infecting a dendritic cell without preventing antigen processing occurring within the infected cell. The attenuated herpes virus and dentrictic cells infected with the virus are useful in immunotherapeutic methods of treating disease.

39 Claims, No Drawings

OTHER PUBLICATIONS

DeLuca et al, "Isolation and Characterization of Deletion Mutants of Herpes Simplex Virus Type 1 in the Gene Encoding Immediate–Early Regulatory Protein ICP4", Journal of Virology 56(2):558–570 (1985).

McFarlane et al, "Hexamethylene bisacetamide stimulates herpes simplex virus immediate early gene expression in the absence of trans–induction by Vmw65", Journal of General Virology 73:285–292 (1992).

Lokensgard et al, "Long–Term Promoter Activity during Herpes Simplex Virus Latency", Journal of Virology 68(11):7148–7158 (1994).

MacLean et al, "Investigation of herpes simplex virus type 1 genes encoding multiply inserted membrane proteins", Journal of General Virology 72:897–906 (1991).

Gossen and Bujard, "Tight control of gene expression in mammalian cells by tetracycline–responsive promoters", Proc. Natl. Acad. Sci. USA 89:5547–5551 (1992).

Smiley and Duncan, "Truncation of the C–Terminal Acidic Transcriptional Activation Domain of Herpes Simplex Virus VP16 Produces a Phenotype Similar to That of the in1814 Linker Insertion Mutation", Journal of Virology 71(8):6191–6193 (1997).

Girolomoni and Ricciardi–Castagnoli, "Dendritic cells hold promise for immunotherapy", Immunology Today 18(3):102–104 (1997).

Dilloo et al, "A Novel Herpes Vector for the High–Efficiency Transduction of Normal and Malignant Human Hematopoietic Cells", Blood 89(1):119–127 (1997).

* cited by examiner

HERPES VIRUS VECTORS FOR DENDRITIC CELLS

FIELD OF THE INVENTION

The present invention relates to attenuated herpes simplex viruses capable of efficiently infecting dendritic cells. It also relates to the use of such viruses in immunotherapy approaches to the treatment of disease.

BACKGROUND TO THE INVENTION

Dendritic cells (DCs) are the most potent antigen presenting cells and are efficient at inducing responses even to antigens to which the immune system has become tolerant. Thus for tumour immunotherapy, in which an immune response is raised against a tumour, the use of DCs may be ideal if they were made to present tumour specific antigens. DCs might also be used to present antigens derived from infectious agents such as bacteria, viruses or parasites, providing protective or therapeutic vaccines for such diseases. However effective transfer of antigens into DCs for any of these targets has proved the greatest problem with this approach.

To provide a realistic chance of generating a therapeutic immune response against a tumour antigen or other disease related antigen, several conditions have to be met. Firstly, it is necessary to identify molecules whose expression is tumour or disease specific (or at least selective), and which can therefore serve as the target for an immune response. This task has proved very difficult for the majority of common tumours, but is solved in for example the case of cervical cancer by the presence, in most cases, of the viral oncogenes E6 and E7, and for other tumours, good candidate antigens are beginning to be identified. For example the MUC-1 gene product is over, expressed in a number of tumours, including 90% of ovarian cancers. Various other tumour associated antigens have also been identified, any of which might be used in an immunotherapy treatment of cancer. Secondly, following the identification of the antigen/antigens, it is necessary to deliver the antigens in an immunogenic form to the immune system. To generate the cellular immune response critical for tumour rejection, this means the proteins must either be delivered inside the cytoplasm of a host cell (a difficult task for high molecular weight protein antigens) or synthesized by the host cells themselves after gene delivery or DNA immunisation. Viral vectors which have been considered for this purpose include vaccinia, adenoviruses, or retroviruses.

The cell-type which is now widely recognised as providing the optimal immune stimulus is the lymphoid dendritic cell (DC; see for example Girolomoni and Ricciardi-Castagnoli, 1997). Indeed the DC appears to be the only cell-type capable of stimulating a primary immune response in vivo, and moreover has even been shown to be capable of breaking established tolerance in certain circumstances. A number of groups are exploring the use of DCs in autologous adoptive immunotherapy protocols to stimulate immune responses against tumours in the hope that they may show a therapeutic effect. Such protocols involve culture and/or enrichment of DCs from peripheral blood, in vitro loading of DCs with antigen, followed by reintroduction of the DCs to the patient However this approach has been hampered by the absence of efficient means by which to load these cells with antigens. Recent work has however shown that presentation of antigens by peptide pulsed DCs has produced anti-tumour responses in vivo (Celluzzi et al., 1996; Zitvogel et al., 1996). As regard to viral vectors, retroviruses do not give high efficiency gene delivery to dendritic cells (Reeves et al., 1996; Aicher et al., 1997), and in our hands, unlike work reported by others (Arthur et al., 1997), adenoviruses only give low efficiency gene delivery.

We have previously tested and reported that herpes simplex viruses (HSV) can efficiently infect and deliver genes to dendritic cells (Coffin et al., 1998), although associated toxicity was not quantified. HSV has a number of advantages over other vector systems for this purpose, in that it can efficiently infect a wide variety of cell-types (including some very hard to infect with other vector systems e.g. Dilloo et al., 1997; Coffin et al., 1998), is easy to manipulate, and can accept large DNA insertions allowing the expression of multiple genes (reviewed by Coffin and Latchman 1996). Delivery of multiple antigens to dendritic cells followed by re-introduction into the body may be a particularly promising approach to the treatment of some cancers and infectious diseases.

SUMMARY OF THE INVENTION

We have previously found that, unlike other vectors in our hands, HSV can efficiently transduce dendritic cells (Coffin et al., 1998), but any toxic effects and the functional capabilities of the transduced dendritic cells were not tested. We have now tested a variety of HSV mutants, from essentially wild type viruses to viruses with mutations either preventing replication in some cell types (mutations in non-essential genes) or all cell types (mutations in essential genes), and some mutants with combinations of deletions in both essential and non-essential genes. We have found considerable differences in both the gene delivery efficiencies of these various mutants and the level of toxicity exhibited (as estimated by dendritic cell death).

Surprisingly we have found that: (i) a virus with inactivating mutations in ICP34.5, VMW65, vhs, and UL43 provides a virus with lower toxicity and higher gene delivery efficiency for dendritic cells than other replication competent viruses tested, including the virus reported previously (Coffin et al., 1998) and also a number of the replication incompetent viruses tested. This is particularly surprising as ICP34.5, VMW65, vhs, and UL43 are all usually regarded as non-essential genes. For example a similar virus including the deletion of one essential gene (mutations in ICP34.5, VMW65, vhs, and ICP27) showed a much lower gene delivery efficiency than this virus. Moreover, unlike the other virus mutants tested, results indicating that efficient antigen processing was occurring could be demonstrated within the target cells. This suggested that transduced dendritic cells retain a functional capability which would allow the stimulation of an effective immune response in vivo. We have also found that (ii) a virus disabled such that only very minimal levels of immediate early genes are expressed in target cells (and thus from which only very low level HSV gene expression generally would be expected) give similar results, unlike other mutants with only a single immediate early gene removed.

These results show that while efficient gene delivery to dendritic cells can be achieved relatively easily using HSV vectors, for the cells to retain their antigen processing capabilities the particular combination of mutations in the virus must be carefully chosen. The invention thus for the first time provides viral vectors for dendritic cells which provide highly efficient gene delivery, without adversely affecting the antigen processing capabilities of the infected dendritic cells.

Thus the present invention provides an attenuated herpes virus capable of efficiently infecting dendritic cells without preventing efficient antigen processing within the infected cell. Preferably said herpes virus is a human herpes simplex virus. More preferably said virus is a herpes simplex virus (HSV), for example HSV1 or HSV2 or a homologous viral strain.

In one embodiment (embodiment (i) above), the herpes virus of the invention typically lacks a functional UL43 gene and a functional vhs gene, if an HSV strain, or their functional equivalents in other viral species. Preferably the virus of the invention also lacks a functional HSV ICP34.5 gene, or its functional equivalent in other viral species. The virus of the invention may also lack a functional VMW65 gene or its functional equivalent in another viral species, especially due to a mutation in said gene which abolishes its transcriptional-activation activity. In a second embodiment (embodiment (ii) above), the herpes virus of the invention contains mutations minimising immediate early gene expression in cells not contemplating the deletions in the virus. Such viruses for example include viruses with inactivating mutations in the genes encoding ICP27 and ICP4 and with an inactivating mutation in the vmw65-encoding gene removing its transactivating function (e.g. vmw65 mutations as in Ace et al., 1989 or Smiley et al 1997). Such viruses also include viruses with inactivating mutations in each of the individual regulatory immediate early genes (encoding ICP4, ICP27, ICP0 and ICP22) with the optional inactivation of the remaining non-regulatory immediate early gene, ICP47.

In preferred embodiments of the present invention, the virus of the invention is either an attenuated HSV strain which comprises a mutation in at least four genes so that it lacks a functional vhs gene, a functional UL43 gene, a functional ICP34.5 gene and a functional VMW65 gene (due to a mutation in said VMW65 gene which abolishes its transcriptional-activation activity), an attenuated HSV strain which comprises mutations so that it lacks at least functional ICP4 gene, a functional ICP27 gene, and a functional vmw65 gene (due to a mutation in said vmw65 gene which abolishes its transcriptional-activation activity) or an attenuated HSV strain which comprises mutations so that it lacks at least a functional ICP4 gene, a functional ICP27 gene, a functional ICP0 gene, and a functional ICP22 gene.

The invention further provides a virus of the invention which carries a heterologous gene/genes. The term heterologous gene is intended to embrace any gene not found in the viral genome. The heterologous gene may be any allelic variant of a wild-type gene, or it may be a mutant gene. Heterologous genes are preferably operably linked to a control sequence permitting expression of said heterologous gene in a dendritic cell, preferably a human dendritic cell. The virus of the invention may thus be used to deliver a heterologous gene to a dendritic cell where it will be expressed.

The heterologous gene/genes preferably encodes a polypeptide of therapeutic use. In particular, the heterologous gene/genes may encode a polypeptide capable of modifying immune responses, for example a cytokine or other immunomodulatory polypeptide. The heterologous gene/genes may also encode an antigenic polypeptide which is present in tumour cells but not non-tumour cells, or up regulated in tumour cells with respect to non-tumour cells. This will be useful in cancer therapy since an infected dendritic cell of the invention can be used to stimulate the host immune system to react to the tumour-specific or tumour-prevalent antigen/antigens resulting in tumour reduction/regression. The polypeptide antigen/antigens is preferably a cell surface polypeptide or a polypeptide that has been engineered so that it will be transported to the cell surface (for example by fusion of a signal peptide). The heterologous gene may also encode a polypeptide/polypeptides of parasitic, viral or bacterial origin so that for example a dendritic cell infected with a virus of the invention can be used to stimulate the host immune system to produce an immune response to a pathogen, either prior to infection or after infection of the host by the pathogen. The heterologous gene/genes may also encode a protein/proteins associated with other diseases (e.g. neurodegenerative diseases such as Huntington's, Alzheimer's or Parkinson's disease) to which it might be beneficial to induce an immune response.

The invention further provides a virus of the invention, carrying a heterologous gene/genes, for use in the treatment of humans and animals, in particular by immunotherapy. For example, such viruses may be used in the treatment or prevention of tumours or parasitic, bacterial or viral infections.

A dendritic cell transduced with a virus of the invention is also provided. Such a cell may be used in an ex vivo method of treating disease, for example malignancies or infection by viral or bacterial pathogens.

DETAILED DESCRIPTION OF THE INVENTION

A. Viruses

An attenuated virus of the invention is capable of efficiently infecting dendritic cells without preventing antigen processing occurring within the infected cell. A virus of the invention is preferably capable of infecting at least 40% of cells at a multiplicity of infection of 1, more preferably at least 50, 60, 70 or 80% of cells. The level/efficiency of expression within an individual cell obtained using a virus of the invention will vary depending on the polypeptide(s) being expressed and the control sequence(s) operably linked to the gene encoding the polypeptide(s) but typically will be at least as efficient as that obtained using a wild type virus. In addition, the virus of the invention exhibits low toxicity towards infected cells. Preferably, cell survival post-infection will be at least 50% at one day post-infection, more preferably at least 60, 70, 80 or 90% at one day post-infection.

To achieve reduced toxicity whilst maintaining efficient infection of and antigen processing in dendritic cells, a virus of the invention will typically lack a functional UL43 gene and a vhs gene (in HSV) or homologues or functional equivalents thereof in other viral species. Additional mutations may be made to reduce further the toxicity of the virus for example by the inclusion of a mutation in the gene encoding vmw65 such as to minimise the transactivating activity of the protein, and/or by the inclusion of an inactivating mutation in the gene encoding ICP34.5. Alternatively, or additionally, the virus will contain mutations which minimise immediate early gene expression from the virus, optionally together with further mutations. Thus a virus of the invention might also typically be mutated in ICP27, ICP4 and with a mutation to vmw65 which minimises the transactivating activity of the protein, or alternatively be mutated for each of the genes encoding ICP4, ICP27, ICP0 and ICP22. A virus of the invention may additionally be mutated for the gene encoding ICP47.

Although the present invention has been exemplified using herpes simplex viruses, it will be understood that other viruses of the herpesviridae family may be modified to achieve reduced toxicity whilst maintaining efficient infection of and antigen processing in dendritic cells. In particular, where gene homologues of the HSV genes described above (especially UL43 and vhs) exist in other herpes virus species, then these homologues will be modified. Alternatively or additionally viruses with mutations to the immediate early genes or with mutations resulting in reduced immediate early gene expression would be especially preferred. By a "homologue" it is meant a gene which exhibits sequence homology, either amino acid or nucleic acid sequence homology, to the corresponding HSV gene. Typically, a homologue of an HSV gene will be at least 15%, preferably at least 20%, identical at the amino acid level to the corresponding HSV gene. For example the prv43 gene of a swine herpes virus, pseudorabies virus, is 23% identical to UL43 (Powers et al., 1994).

Methods of measuring nucleic acid and protein homology are well known in the art. For example the UWGCG Package provides the BESTFIT program which can be used to calculate homology (Devereux et al (1984) *Nucleic Acids Research* 12:387–395).

Similarly, the PILEUP and BLAST algorithms can be used to line up sequences (for example as described in Altschul S. F. (1993) *J. Mol. Evol.* 36:290–300; Altschul, S. F. et al (1990) *J. Mol. Biol.* 215:403–10). Software for performing BLAST analysis is publicly available through the National Center for Biotechnology Information (http://www.ncbi.nlm.nih.gov/).

Many different settings are possible for such programs. According to the invention, the default settings may be used.

Homologues of HSV genes can be identified in a number of ways, for example by probing genomic or cDNA libraries made from other viruses with probes comprising all or part of the HSV gene under conditions of medium to high stringency (for example 0.03M sodium chloride and 0.03M sodium citrate at from about 50° C. to about 60° C.). Alternatively, species homologues may also be obtained using degenerate PCR which will use primers designed to target sequences within the variants and homologues encoding conserved amino acid sequences. The primers will contain one or more degenerate positions and will be used at stringency conditions lower than those used for cloning sequences with single sequence primers against known sequences (for example 0.03M sodium chloride and 0.03M sodium citrate at about 40° C.).

For reasons of safety, the viruses of the invention are attenuated, typically so that they are incapable of replicating efficiently in the target cell. Viral regions altered for the purposes of attenuation may be either eliminated (completely or partly), or made non-functional, or substituted by other sequences, in particular by a heterologous gene sequence. Attenuating mutations have been described for all viral groups used as viral vectors. For example, HSV may be rendered avirulent by mutations in ICP34.5 and/or essential genes such as ICP4 and ICP27.

1. Herpes Simplex Viruses i. Viruses

When the virus of the invention is a herpes simplex virus, the virus may be derived from, for example, HSV1 or HSV2 strains, or derivatives thereof, preferably HSV1. Derivatives include inter-type recombinants containing DNA from HSV1 and HSV2 strains. Derivatives preferably have at least 70% sequence homology to either the HSV1 or HSV2 genomes, more preferably at least 80%, even more preferably at least 90 or 95%, typically as measured by the methods described herein. Other derivatives which may be used to obtain the viruses of the present invention include strains that already have mutations in genes which it is desired to functionally inactivate in a virus of the invention, for example strain 1716 (MacLean et al., 1991), strains R3616 and R4009 (Chou and Roizman, 1992) and R930 (Chou et al., 1994) all of which have mutations in ICP34.5, strain d120 which has a deletion in ICP4 (DeLuca et al., 1985), strain d27-1 (Rice and Knipe, 1990) which has a deletion in ICP27) or strain d92 which has deletions in both ICP27 and ICP4 (Samaniego et al., 1995). Use of these strains will reduce the number of steps required to produce the mutant HSV strains of the present invention.

The terminology used in describing the various HSV genes is as found in Coffin and Latchman, 1996.

ii. Complementing Cell Lines

When the herpes simplex viruses of the invention lacks a particular functional essential gene, for example a gene encoding ICP4 or ICP27, the virus of the invention is propagated using a cell line expressing that essential gene. For example, when the virus lacks a functional ICP27 gene, the virus may be propagated using V27 cells (Rice and Knipe, 1990), 2-2 cells (Smith et al., 1992) or B130/2 cells (WO98/30707), preferably B130/2 cells. When the virus lacks a functional ICP4 gene the virus may be propagated using a cell line expressing ICP4, for example E5 cells (DeLuca et al., 1985). When the virus lacks a functional ICP4 gene and a functional ICP27 gene the virus is propagated using a cell line expressing both ICP4 and ICP27 (such as E26 cells; Samaniego et al., 1995), and when the virus additionally lacks a functional vmw65 gene the virus may be propagated using a cell line also containing a non-HSV hornologue of vmw65 (e.g. equine herpes virus gene 12 or BTIF from bovine herpes virus).

ICP27-expressing cell lines can be produced by co-transfecting mammalian cells, for example the Vero or BHK cells, with a vector, preferably a plasmid vector, comprising a functional HSV ICP27 gene capable of being expressed in said cells, and a vector, preferably a plasmid vector, encoding a selectable marker, for example neomycin resistance. Clones possessing the selectable marker are then screened further to determine which clones also express functional ICP27, for example on the basis of their ability to support the growth of $ICP27^-$ HSV strains, using methods known to those skilled in the art (for example as described in Rice and Knipe, 1990).

Cell lines which do not allow reversion of an $ICP27^-$ mutant HSV strain to a strain with functional ICP27 are produced as described above, ensuring that the vector comprising a functional ICP27 gene does not contain sequences that overlap with (i.e. are homologous to) sequences remaining in the $ICP27^-$ mutant virus.

Where HSV strains of the invention comprise inactivating modifications in other essential genes, for example ICP4, complementing cell lines will comprise a functional HSV gene which complements the modified essential gene in the same manner as described for ICP27. For example in the case of HSV strains comprising mutations in both ICP27 and ICP4, a cell line expressing both ICP27 and ICP4 is used (such as E26 cells (Samaniego et al., 1995). HSV strains expressing other essential genes can be constructed in a similar manner to that described for ICP27.

B. Methods of Mutation

The various viral genes referred to may be rendered functionally inactive by several techniques well known in the art. For example, they may be rendered functionally inactive by deletions, substitutions or insertions, preferably by deletion. Deletions may remove portions of the genes or the entire gene. For example, deletion of only one nucleotide may be made, resulting in a frame shift. However, preferably larger deletions are made, for example at least 25%, more preferably at least 50% of the total coding and non-coding sequence (or alternatively, in absolute terms, at least 10 nucleotides, more preferably at least 100 nucleotides, most preferably, at least 1000 nucleotides). It is particularly preferred to remove the entire gene and some of the flanking sequences. Inserted sequences may include the heterologous genes described below. In particular, it is preferred to insert the heterologous gene into ICP27 or ICP4. In the case of the VMW65 gene, the entire gene is not deleted since it encodes an essential structural protein, but a small inactivating mutation is made which abolishes the ability of VMW65 to activate transcriptionally IE genes (e.g. as in Ace et al., 1989 or Smiley et al., 1997).

Mutations are made in the herpes viruses by homologous recombination methods well known to those skilled in the art. For example, HSV genomic DNA is transfected together with a vector, preferably a plasmid vector, comprising the mutated sequence flanked by homologous HSV sequences. The mutated sequence may comprise deletions, insertions or substitutions, all of which may be constructed by routine techniques. Insertions may include selectable marker genes, for example lacZ or GFP, for screening recombinant viruses by, for example, α-galactosidase activity or fluorescence.

C. Heterologous Genes and Promoters

The viruses of the invention may be modified to carry a heterologous gene/genes. The term "heterologous gene" encompasses any gene. Although a heterologous gene is typically a gene not present in the genome of a herpes virus, herpes gene may be used provided that the coding sequence is not operably linked to the viral control sequences with which it is naturally associated. The heterologous gene may be any allelic variant of a wild-type gene, or it may be a mutant gene. The term "gene" is intended to cover nucleic acid sequences which are capable of being at least transcribed. Thus, sequences encoding mRNA, tRNA and rRNA are included within this definition. However, the present invention is concerned with the expression of polypeptides rather than tRNA and rRNA. Sequences encoding mRNA will optionally include some or all of 5' and/or 3' transcribed but untranslated flanking sequences naturally, or otherwise, associated with the translated coding sequence. It may optionally further include the associated transcriptional control sequences normally associated with the transcribed sequences, for example transcriptional stop signals, polyadenylation sites and downstream enhancer elements.

The heterologous gene/genes may be inserted into the viral genome by homologous recombination of HSV strains with, for example, plasmid vectors carrying the heterologous gene/genes flanked by HSV sequences. The heterologous gene/genes may be introduced into a suitable plasmid vector comprising herpes viral sequences using cloning techniques well-known in the art. The heterologous gene/genes may be inserted into the viral genome at any location provided that the virus can still be propagated. It is preferred that the heterologous gene/genes is inserted into an essential gene. Heterologous genes may be inserted at multiple sites within the virus genome.

The transcribed sequence of the heterologous gene/genes is preferably operably linked to a control sequence permitting expression of the heterologous gene/genes in dendritic cells, preferably mammalian dendritic cells, more preferably human dendritic cells. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequence.

The control sequence comprises a promoter allowing expression of the heterologous gene/genes and a signal for termination of transcription. The promoter is selected from promoters which are functional in mammalian, preferably human dendritic cells. The promoter/promoters may be derived from promoter sequences of eukaryotic genes. For example, promoters may be derived from the genome of a cell in which expression of the heterologous gene is to occur, preferably a mammalian dendritic cell or more preferably a human dendritic cell. With respect to eukaryotic promoters, they may be promoters that function in a ubiquitous manner (such as promoters of β-actin, tubulin) or, alternatively, a tissue-specific manner (such as promoters of the genes for pyrurate kinase). They may also be promoters that respond to specific stimuli, for example promoters that bind steroid hormone receptors. Viral promoters may also be used, for example the Moloney murine leukaemia virus long terminal repeat (MMLV LTR) promoter or promoters of herpes virus genes.

The HSV LAT promoter, and promoters containing elements of the LAT promoter region, may be especially preferred because there is the possibility of achieving long-term expression of heterologous genes during latency. In particular, an expression cassette consisting essentially of a LAT P2 region, which does not itself here act as a promoter, linked to a promoter and a heterologous gene in that order is especially preferred.

The term "long-term expression" is taken to mean expression of a heterologous gene in a cell infected with a herpes simplex virus of the invention even after the herpes simplex virus has entered latency. Preferably, this is for at least two weeks, more preferably at least one or two months after infection, even more preferably for the life-time of the cell.

Expression cassettes may further comprise a second promoter and a second heterologous gene operably linked in that order to said HSV LAT P2 region and in the opposite orientation to the first promoter and first heterologous gene wherein said second promoter and second heterologous gene are the same as or different to the first promoter and first heterologous gene. Thus a pair of promoter/heterologous gene constructs in opposite orientations flank a single LAT P2 region allowing the long term expression of pairs of heterologous genes, which may be the same or different, driven by the same or different promoters. Furthermore, the product of the first heterologous gene may regulate the expression of the second heterologous gene (or vice-versa) under suitable physiological conditions.

Expression cassettes and other suitable constructs comprising the heterologous gene/genes and control sequences can be made using routine cloning techniques known to persons skilled in the art (see, for example, Sambrook et al., 1989, Molecular Cloning—a laboratory manual; Cold Spring Harbor Press). The LAT P2 region is here defined as HSV1 nucleotides 118866–120219 of HSV strain 17+ (GenBank HE1CG: from PstI-BstXI sites), and includes fragments or derivatives of this region, including homologous regions of other HSV1 strains and of HSV2 strains, which are capable of providing a long-term expression capability to promoters to which they are linked.

It may also be advantageous for the promoters to be inducible so that the levels of expression of the heterologous gene can be regulated during the life-time of the cell. Inducible means that the levels of expression obtained using the promoter can be regulated. For example, in a preferred embodiment where more than one heterologous gene is inserted into the HSV genome, one promoter would comprise a promoter responsive to the tet repressor/VP16 transcriptional activator fusion protein previously reported (Gossen and Bujard, 1992, Gossen et al, 1995), and driving the heterologous gene the expression of which is to be regulated. The second promoter would comprise a strong promoter (e.g. the CMV IE promoter) driving the expression of the tet repressor/VP16 fusion protein. Thus in this example expression of the first heterologous gene would depend on the presence or absence of tetracycline.

In addition, any of these promoters may be modified by the addition of further regulatory sequences, for example enhancer sequences (including elements of the HSV LAT region). Chimeric promoters may also be used comprising sequence elements from two or more different promoters described above, for example an MMLV LTR/LAT fusion promoter (Lokensgard et al., 1994) or promoters comprising elements of the LAT region (see above).

Heterologous genes will typically encode polypeptides of therapeutic use. For example, to promote an immune response specifically against a particular tumour, it will be desirable to transfect dendritic cells with a virus of the invention directing expression of a tumour antigen/antigens. A tumour antigen may be specific to a tumour cell or it may be present at higher levels in that tumour cell than in a non tumour cell of that type, for example due to up regulation of expression of the antigen. In particular, it is preferred that the tumour antigen/antigens is expressed on the surface of the tumour cell, for example a cell surface receptor or cell adhesion protein. Examples of tumour antigens include the MUC-1 gene product (Gendler et al., 1990) which is over expressed in a number of tumours including ovarian cancers, human papillomavirus proteins E6 and E7 which are associated with cervical cancer. Tumour antigens that elicit T-cell responses are particularly preferred.

Heterologous genes may also encode a polypeptide which is capable of modifying an immune response, for example cytokines (such as $\alpha$-, $\beta$- or $\gamma$-interferon, interleukins including IL-1, IL-2, tumour necrosis factor, or insulin-like growth factors I or II) or other immunomodulatory proteins.

Heterologous genes may also encode antigenic polypeptides for use as vaccines. Preferably such antigenic polypeptides are derived from pathogenic organisms, for example parasites, bacteria or viruses. Examples of such antigenic polypeptides include hepatitis C virus antigens, hepatitis B surface or core antigens, HIV antigens, malaria antigens, pertussis toxin, cholera toxin or diphtheria toxin.

Heterologous genes may also include marker genes (for example encoding $\beta$-galactosidase or green fluorescent protein) or genes whose products regulate the expression of other genes (for example, transcriptional regulatory factors including the tet repressor/VP16 transcriptional activator fusion protein described above).

Gene therapy and other therapeutic applications may well require the administration of multiple genes. The expression of multiple genes may be advantageous for the treatment of a variety of conditions. Herpes viruses are uniquely appropriate as they do not have the limited packaging capabilities of other viral vector systems. Thus multiple heterologous genes can be accommodated within its genome. There are, for example, at least two ways in which this could be achieved. For example, more than one heterologous gene and associated control sequences could be introduced into a particular HSV strain either at a single site or at multiple sites in the virus genome. It would also be possible to use pairs of promoters (the same or different promoters) facing in opposite orientations away from each other, these promoters each driving the expression of a heterologous gene (the same or different heterologous gene) as described above.

D. Dendritic Cells

Dendritic cells can be isolated/prepared by a number of means, for example they can either be purified directly from peripheral blood, or generated from CD34+ precursor cells for example after mobilisation into peripheral blood by treatment with G-CSF, or directly from bone marrow. From peripheral blood adherent precursors can be treated with a GM-CSF/IL-4 mixture (Inaba et al., 1992), or from bone marrow non-adherent CD34+ cells can be treated with GM-CSF and TNF-$\alpha$ (Caux et al., 1992). DCs can be routinely prepared from the peripheral blood of human volunteers, similarly to the method of Sallusto and Lanzavecchia, 1994, using purified peripheral blood mononeucleocytes (PBMCs) and treating 2 hour adherent cells with GM-CSF and IL-4. These are then depleted of CD19+ B cells and CD3+, CD2+ T cells using magnetic beads (see Coffin et al., 1998). Other methods may also be used for the preparation of dendritic cells.

E. Therapeutic Uses

Viruses of the invention, and dendritic cells infected with viruses of the invention may be used in methods of therapy. In particular, viruses of the invention, and dendritic cells infected with viruses of the invention, which express tumour antigens may be used in methods of treating cancer. Specifically, the, viruses of the invention, and dendritic cells infected with viruses of the invention may be used to inhibit the growth of various tumours in mammals, including humans, such as, for instance, ovarian, cervical and endometrial tumours and carcinomas, for example mammary carcinoma, lung carcinoma, bladder carcinoma and colon carcinoma. Other neoplasms whose growth may be inhibited include sarcomas, for example soft tissue and bone sarcomas, and hematological malignancies such as leukemias. Particular examples of cancers which may be treated using viruses of the invention and/or dendritic cells infected with viruses of the invention which express tumour antigens include melanomas, leukemias, cervical cancers and ovarian cancers.

Viruses of the invention, and dendritic cells infected with viruses of the invention may be used in methods of treating or preventing pathogenic infections, for example parasitic, bacterial or viral infections. In this case, the viruses/dendritic cells may be administered prior to infection to stimulate a protective immune response in the host, or after infection to stimulate the host immune system to combat the infection.

F. Administration

The herpes viruses of the present invention may thus be used to deliver therapeutic genes to a human or animal in need of treatment. Delivery of therapeutic genes using the herpes viruses of the invention may be used to treat for example, malignancies and pathogenic infections.

One method for carrying out therapy involves inserting the therapeutic gene/genes into the genome of the herpes virus of the invention, as described above, and then combining the resultant recombinant virus with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous or transdermal administration.

Infection of dendritic cells with the virus of the invention may be carried out in vivo by administration of a composition comprising the virus to a patient. The pharmaceutical composition is administered in such a way that the virus containing the therapeutic gene/genes, can be incorporated into cells at an appropriate area. The amount of virus administered is in the range of from $10^4$ to $10^{10}$ pfu, preferably from $10^5$ to $10^8$ pfu, more preferably about $10^6$ to $10^7$ pfu. When injected, typically from 10 µl to 1 ml, preferably from 100 µl to 1 ml of virus in a pharmaceutically acceptable suitable carrier or diluent is administered.

Another method involves isolating/preparing dendritic cells from peripheral blood or bone marrow and infecting the cells with the virus of the invention in vitro. Transduced dendritic cells are then typically administered to the patient by intramuscular, intraperitoneal, subcutaneous or intravenous injection, or by direct injection into the lymph nodes of the patient, preferably by direct injection into the lymph nodes. Typically from $10^4$ to log transduced dendritic cells, preferably from $10^5$ to $10^7$ cells, more preferably about $10^6$ cells are administered to the patient.

The routes of administration and dosages described are intended only as a guide since a skilled practitioner will be able to determine readily the optimum route of administration and dosage for any particular patient depending on, for example, the age, weight and condition of the patient.

The invention will be described with reference to the following Examples, which are intended to be illustrative only and not limiting.

EXAMPLES

Materials and Methods

Construction and Growth of Viral Strains

All virus strains are derived from HSV1 strain 17+, the nucleotide sequence of which is deposited in GenBank (Accession No. HE1CG). All strains were produced and propagated using BHK C-21 cells (ECACC No. 8501143), apart from strains 17+/27−/pR20 and 1764/27−/pR20.5/vhs which were grown on B130/2 cells (BHK cells stably transfected with the HSV1 ICP27 gene) and strain 1764/27−4−/pR20.5 which was propagated using cells stably transfected with the genes encoding HSV1 ICP27, ICP4 and equine herpes virus gene 12. EHV gene 12 is the EHV homologue of HSV vmw65 which we have found when included in cell lines can compensate for growth deficiencies associated with vmw65 mutation, although the EHV gene 12 protein product is not then packaged into resulting HSV virions as would be the case if un-altered HSV vmw65 were included in the cells used for virus growth. Such cells were generated as follows: BHK cells (grown in DMEM+10% FCS, both Gibco, at 37° C./5%CO2) were transfected (by the method of Gorman, 1985) in 10 cm plates with plasmids containing EHV-gene 12 (Lewis J B, et al. (1997) Virology, 230, 369–375) under the control of a CMV promoter and BGHpA sequence (pcDNA3/E) and a plasmid encoding ICP27 (pSG130BS [Sekulovich et al 1988]). After selection with neomycin, neomycin resistant clones were selected and assessed for their ability to support the growth of HSV mutated for ICP27 and vmw65 and a highly permissive clone selected. To introduce ICP4, a phleomycin/neomycin resistant cell line was produced from these BHK cells containing EHV gene 12 and ICP27 in which ICP4 was driven by the dexamethasone inducible MMTV promoter and an SV40 polyA (using plasmid pMAMzeo/ICP4). For construction of pMAMzeo/ICP4 the neomycin resistance gene (excised as a BamHI fragment) in plasmid pMAMneo (Invitrogen) was replaced by the phleomycin resistance gene, as a BamHI fragment from pVgRXR (Invitrogen). The ICP4 coding region (HSV1 nts 127,167–131,187 [MseI-BstEII] GenBANK file he1 cg) was then inserted after the MMTV promoter at the XhoI site. A clone highly permissive for the growth of HSV mutated for ICP4, ICP27 and vmw65 was then selected following transfection into the ICP27/EHV gene 12 containing cells and selection with phleomycin (Zeocin; Cayla, Toulouse, France).

For viruses with mutations in VMW65, 3 mM hexamethylene-bisacetamide (HMBA) was included in the media used for virus growth (McFarlane et al., 1992).

(i) 17+/pR20.5/UL43

A cassette from plasmid pR20.5 consisting of an RSV/lacZ/pA sequence and a CMV/GFP/pA sequence in opposite back-to-back orientations and separated by an HSV LAT region sequence (nts 118,866–120,219) was inserted into the UL43 locus by homologous recombination with purified genomic HSV1 strain 17+ DNA by standard methods. The pR20.5 cassette was first inserted into a plasmid containing UL43 flanking regions (Coffin et al, 1996) at the unique NsiI site, giving plasmid pR20.5/43. The 20.5 cassette can be excised from it's pGEM5 (Promega) plasmid backbone with SrfI as an oligonucleotide encoding SrfI was inserted on either side of the cassette. The RSV promoter was excised from pRc/RSV (Invotrogen), lacZ/pA from pCH110 (Pharmacia), CMV/pA from pcDNA3 (Invitrogen) and GFP from pEGFP-N1 (Clontech) for the construction of plasmid pR20.5.

(ii) 17+/pR20.5/US5

The pR20.5 cassette was inserted into the US5 locus of HSV1 by insertion of the pR20.5 cassette into US5 flanking regions (plasmid pΔUS5) generating plasmid pR20.5/US5 followed by homologous recombination together with purified genomic HSV1 strain 17+ DNA into BHK cells giving virus strain 17+/pR20.5/US5. Plasmid pΔUS5 was prepared by clonmg a BamHI-EcoNI fragment (nts 136,289–131,328) from HSV1, which includes the US5 coding region, into plasmid pAT153. pR20.5 was inserted into a unique SacI site at nt 137,945 in the US5 gene.

(iii) 17+/27−/pR20

Plasmid pR20 was used for homologous recombination into purified HSV strain 17+ DNA. Plasmid pR20 contains a LAT P2 (HSV1 nts 118866–120219)/CMV/lacZ cassette inserted into ICP27 flanking regions (HSV1 nts 11095–113273 and nts 116869–118439 in pACYC184 [NBL] allowing insertion at the unique MluI site which joins the two fragments). LacZ expressing plaques were purified using B130/2 cells.

(iv) 1764/pR20.5/UL43

Plasmid pR20.5/43 was used for homologous recombination into purified HSV strain 1764 DNA (Coffin et al., 1996) and plaque purification of GFP and LacZ expressing plaques. Strain HSV 1764 is strain 17+ from which both copies of ICP34.5 have been deleted and with an inactivating mutation in the gene for VMW65 (Ace et al., 1989).

(v) 1764/pR20.5/US5

Plasmid pR20.5/5 was used for homologous recombination into purified HSV strain 1764 DNA and plaque purification of GFP and LacZ expressing plaques.

(vi) in1814/pR15

Plasmid pR15 was used for homologous recombination into the gene for the virion host shutoff protein (UL41) of strain in1814 (Ace et al., 1989). Plasmid pR15 contains vhs flanking regions with the insertion of a lacZ gene driven by an HSV LAT/MMLV LTR chimaeric promoter (essentially identical to that reported by Lokensgard et al., 1994) at the unique NruI site in the UL41 gene. LacZ expressing plaques were purified.

(vii) 1764/pR15

Plasmid pR15 was used for homologous recombination into purified HSV strain 1764 DNA, and lacZ expressing plaques purified.

(viii) 1764/27−/pR20.5/vhs

The pR20.5 cassette was inserted into vhs flanking regions at the unique NruI site, and the resulting plasmid (pR20.5/vhs) used for homologous recombination into purified HSV strain 1764/27−DNA. Plaques expressing both lacZ and GFP were purified using B130/2 cells. Strain 1764/27− was generated from strain 1764/27−/pR20 (generated by homologous recombination of plasmid pR20 into HSV strain 1764 DNA and selection of lacZ expressing plaques) by homologous recombination to remove the lacZ gene, deleting nucleotides 113322–115743 around the ICP27 locus.

(ix) 1764/pR15/MSVGFP/UL43

An MSV LTR promoter/GFP cassette was inserted into UL43 flanking regions at the unique NsiI site, giving plasmid pMSVGFP/43. pMSVGFP/43 was then used for homologous recombination into purified HSV strain 1764/pR15 genomic DNA, and plaques expressing both lacZ and GFP purified.

(x) 1764/27−/4−/pR20.5

Virus strain 1764/27−/4−/pR20.5 was constructed by insertion of a cassette consisting of GFP (E-GFP; Clontech) and lacZ driven by CMV and RSV promoters respectively in a back-to-back orientation and separated by HSV1 LAT sequences (PstI-BstXI−: nts 118,866–120,219 [PstI-BstXI] GenBank file he1 cg) to ICP4 flanking regions (HSV1 nts 123,459–126,774 [Sau3aI-Sau3aI] and 131,730–134,792 [SphI-KpnI] with nts 124,945–125,723 [NotI-NotI; encodes ICP34.5] deleted separated by unique XbaI and SalI sites in plasmid pDICP4) and recombination into virus strain 1764/27−(see above) using B4/27 cells which complement both ICP27 and ICP4. X-gal staining/green fluorescent plaques were selected and further purified. Cell line B4/27 was prepared by co-transfection of pSG130BS, plasmid p4/2 (encoding ICP4 coding, promoter and poly A regions) and pMAMneo (Invitrogen) into BHK cells. Neomycin resistant clones were then selected.

Example 1

Genes Can Be Efficiently Delivered to Dendritic Cells Using HSV Vectors

These experiments were aimed to determine if HSV could infect and deliver genes to dendritic cells, using essentially wild type viruses. Multiplicities of infection (MOI) of between 0.1 to 10 were used. Here in each case $1 \times 10^5$ dendritic cells were infected by gentle pelleting, resuspension in about 100 µl virus suspension in DMEM, incubation at 37° C. for 1 hr, then transfer into 24 well plates with 2 ml of RPMI/10%FCS+100 ng/ml GM-CSF, 50 ng/ml IL-4. These plates were then incubated at 37° C./5% $CO_2$ for the remainder of the experiment. Viruses 17+/pR20.5/UL43 and 17+/pR20.5/US5 were used for these experiments, each mutated for a different gene (UL43 or US5) by the insertion of the pR20.5 cassette. Both UL43 and US5 have been previously identified as being unnecessary for growth of HSV in culture, and as not affecting the kinetics of infection in mouse models in vivo. The efficiency of gene delivery was assessed by counting GFP positive cells under fluorescence microscopy 24 hrs after infection. The results shown below in Table 1 demonstrate that HSV can efficiently deliver genes to dendritic cells.

TABLE 1

| | Results | |
|---|---|---|
| | % Gene delivery | |
| MOI | 17+/pR20.5/UL43 | 17+/pR20.5/US5 |
| 0.1 | 10 | 11 |
| 0.5 | 15 | 30 |
| 1 | 45 | 45 |
| 5 | 65 | 55 |
| 10 | 85 | 75 |

Example 2

Dendritic Cells Are Relatively Non-permissive for the Growth of HSV, Inactivation of UL43 Reducing Growth Further To determine whether the efficient gene delivery observed in Example 1 was due to lytic replication of the viruses, growth curves were performed in which dendritic cells were infected at MOIs ranging from 0.1 to 10, as in Example 1, and virus growth quantified over time. At 24 hr intervals samples of the culture media were titred onto BHK cell—permissive for the growth of HSV—and numbers of plaques counted.

TABLE 2

| | Results | | | | | |
|---|---|---|---|---|---|---|
| | Total virus in dendritic cell culture media (pfu) | | | | | |
| Time after infection | 17+/pR20.5/UL43 MOI | | | 17+/pR20.5/US5 MOI | | |
| (days) | 0.1 | 1 | 10 | 0.1 | 1 | 10 |
| 0 | 10000 | 100000 | 1000000 | 10000 | 10000 | 1000000 |
| 1 | 200 | 100000 | 300000 | 100 | 100000 | 10000 |
| 2 | 2000 | 10000 | 60000 | 10000 | 40000 | 8000 |
| 3 | 20000 | 1000 | 20000 | 300000 | 30000 | 2000 |
| 4 | 1000 | 1000 | 10000 | 100000 | 20000 | 2000 |

As shown in Table 2 above, these experiments demonstrated that while a limited productive infection can occur in dendritic cell cultures infected with HSV this is only apparent at low MOI (particularly the US5 deleted virus). Inactivation of UL43 instead of US5 reduces this limited productive infection further. It appears that a slow turn-over of wild-type HSV can occur in dendritic cell cultures, which is reduced by inactivation of UL43, but that this is not accompanied by significant dendritic cell death (see Example 3). Inactivation of UL43 has previously not been found to affect the growth kinetics of HSV (Maclean et al., 1991).

Example 3

Different HSV Mutants Show Different Levels of Gene Delivery Efficiency and Toxicity in Dendritic Cells The virus strains (i)–(x) described above were used to infect dendritic cells at MOI's in a range between 0.1–10 as in Example 1. At intervals duplicate samples (2×100 µl of the culture) were taken and one sample viewed for GFP expression (fluorescence microscopy) and/or stained with X-gal by gentle pelleting and resuspension in fix (0.8% glutaraldehyde for 10 min) followed by X-gal buffer (as in Coffin et al., 1996) and incubation at 37° C. for 2 hr, depending on the nature of the insertion in the particular virus under test. The other sample was stained with trypan blue-live cells excluding the stain, and the number of non-staining cells as a percentage of the number of cells in the original culture counted. In each individual set of experiments, which were repeated twice and in which usually three viruses were tested at a time, virus (i) was used as an internal control to allow for any variations between dendritic cell preparations. Results are shown for MOI=1.

Example 4

HSV with Inactivating Mutations in UL43, ICP34.5, vhs and VMW65 Gives Results which Indicate that Efficient Proteolytic Processing of Delivered Antigen Is Occurring in Transduced Dentritic Cells The virus deleted for UL43, ICP34.5, vhs and VMW65, gave highly efficient delivery of GFP. LacZ activity on the other hand, while present in many cells, was only present at a very low level 24 hrs after infection, at the limits of

TABLE 3

| Genes inactivated (X) | Results Virus | | | | | | | | | | Control |
|---|---|---|---|---|---|---|---|---|---|---|---|
| | (i) | (ii) | (iii) | (iv) | (v) | (vi) | (vii) | (viii) | (ix) | (x) | (No virus) |
| UL43 | X | | | X | | | | | X | | |
| US5 | | X | | | X | | | | | | |
| VMW65 | | | | X | X | X | X | X | X | X | |
| ICP27 | | | X | | | | | X | | X | |
| Vhs | | | | | | X | X | X | | | |
| ICP34.5 | | | | X | X | | X | X | X | X | |
| ICP4 | | | | | | | | | | X | |
| % Gene delivery 1 day (lacZ/GFP) | 45/45 | 45/45 | 3/– | 70/70 | 70/70 | 35/– | 30/– | 15/15 | +/85 | 20/257 | — |
| % Cell survival 1 day | 85 | 84 | 90 | 75 | 70 | 58 | 70 | 90 | 90 | 92 | 99 |
| % Cell survival 4 days | 60 | 50 | ND | 41 | 47 | 38 | 45 | ND | 65 | 80 | 82 |

*many cells stain blue with X-gal, but blue staining of very low intensity.
Exact quantification not possible
Z see Example 5
ND not done Viruses (see materials and methods): (i) 17+/pR20.5/UL43, (ii) 17+/pR20.5/US5, (iii) 17+/27–/pR20, (iv) 1764/pR20.5/US5, (v) 1764/pR20.5/UL43, (vi) in1814/pR15, (vii) 1764/pR15, (viii) 1764/27–/pR20.5/vhs, (ix) 1764/pR15/MSVGFP/UL43, (x) 1764/27–/4–/pR20.5.

These results showed that different combinations of gene deletions provided viruses with various combinations of gene delivery efficiency and lack of toxicity, some improved for one or other or both characteristics as compared to the, original viruses (i) and (ii), and others in which either gene delivery efficiency or cell survival was reduced. Removal of one essential immediate early gene (ICP27) appeared to give viruses which were apparently minimally toxic, but in which gene delivery efficiency was considerably reduced. A virus with a combination of non-essential genes inactivated. (ICP34.5, VMW65, vhs and UL43), each of which has previously been shown to reduce virulence in vivo individually (other than UL43) was found to give the best combination of gene delivery efficiency (for GFP at least, see Example 4) and lack of toxicity, this gene delivery efficiency being considerably greater than with any of the other viruses tested. However, virus (x), which was also minimally toxic was shown to give high level GFP and lacZ RNA expression (see below), similar in level to virus (ix) even though less GFP could be detected by fluorescence. However virus (x), which was also minimally toxic was shown to give high level GFP and lacZ RNA expression (see below), similar in level to virus (ix) even though less GFP could be detected by fluorescence. Western blots using anti-HSV ICP27, ICP4, ICP0, ICP22 and ICP47 antibodies have previously shown this virus expresses only very low levels of any immediate early gene on cells which do not complement the deficiencies in the virus (i.e. the mutations in ICP27, ICP4 and vmw65).

detection with X-gal staining. This raised the possibility that both lacZ and GFP were produced efficiently in the cells, but that apparent lacZ activity was being reduced by efficient proteolytic processing of the lacZ antigen—as might be expected in a fully functional dendritic cell. The lacZ gene is transcribed from an identical promoter to that in others of the viruses which do give strong X-gal staining in dendritic cells. Thus if processing of the lacZ is occurring within the cells both lacZ mRNA and GFP mRNA should be easily detectable at relatively equal levels by northern blotting, but the lacZ protein levels by western blotting should be markedly reduced.

Northern and western blots were performed using RNA and protein (extracted from $1 \times 10^5$ cells/lane in each case) from dendritic cells infected with either 17+/pR20.5/UL43 or 1764/pR15/MSVGFP/UL43 at an MOI of 1. Western blots were then probed with either an anti-LacZ antibody (Promega) or an anti-GFP antibody (Quantum). Northern blots were probed with the LacZ gene (excised from pCH110 (Pharmacia) with HindIII and BamHI) or the GFP gene (excised from pEGFP-N1 (Clontech) with NotI and HindIII). Northern and western blots were performed by standard methods (Sambrook et al. 1989) by radioactive (northern blots) or non-radioactive (western blots; ECL, Amersham) means.

Results

Western blots showed:
(i) Efficient detection of both lacZ and GFP in dendritic cells infected with 17+/pR20.5/UL43. A single defined band was observed at the expected molecular weight in each case, with some smaller fainter bands also visible.
(ii) As expected with the X-gal staining, while GFP was easily detected with 1764/pR15/MSV/GFP/UL43, lacZ protein levels at the expected molecular weight were significantly reduced.

Northern blots showed a strong, defined band of the expected size in each case, whether cells were infected with 17+/pR20.5/UL43 or 1764/pR15/MSVGFP/UL43.

These results demonstrate that while lacZ mRNA is efficiently produced in dendritic cells following infection with both 1764/pR15/MSVGFP/UL43 and 17+/pR20.5/UL43, for 1764/pR15/MSVGFP/UL43 this RNA is either not translated or the lacZ protein is rapidly degraded after translation so that the levels of full length protein detectable by western blotting are significantly reduced. Considering the role of dendritic cells in antigen processing, the latter is likely to be the case as this would be expected if such a delivered antigen were processed in an efficient manner. Such efficient antigen processing thus does not occur with the other mutants tested (other than in Example 5 below), as strong X-gal staining can be seen in each case. Thus for antigen processing of a virally delivered antigen to occur in dendritic cells, the precise choice of virus mutant used for delivery must be carefully chosen.

Example 5

HSV from which Only Minimal Immediate Early Gene Expression Is Possible Also Allow Efficient, Low-toxicity Gene Delivery to Dendritic Cells and Give Results which Indicate that Processing of Delivered Antigen Is Occurring in Transduced Dendritic Cells As in example 4 above, comparative western and RNA blots were performed (here for RNA using slot blots). LacZ and GFP protein and RNA levels in extracts of dendritic cells infected with 17+/pR20.5/UL43, 1764/pR15/MSVGFP/UL43 or 1764/27−/4−/pR20.5 were compared.

Results

The results of this experiment were as in example 4 except for 1764/27−4−/pR20.5 infected cells. Here, while equivalent levels of GFP and lacZ RNA could be detected as with 17+/pR20.5/UL43 and 1764/pR15/MSVGFP/UL43 infected cells, only relatively low level GFP could be detected by western blotting, considerably less than with 17+/pR20.5/UL43 or 1764/pR15/MSVGFP/UL43. Thus in the case of 1764/27−/4−/pR20.5 lower levels of both lacZ and GFP protein could be detected (rather than only lower levels of lacZ protein with1764/pR15/MSVGFP/UL43 as previously in example 4), than would be expected bearing in mind the amount of lacZ and GFP specific RNA present which was similar with all the viruses tested in examples 4 and 5. This result is indicative that unlike with any of the other viruses tested, following gene delivery with 1764/27−/4−/pR20.5, both lacZ and GFP are undergoing proteolytic processing such as might be expected in a functional dendritic cell. This suggests further functionality over and above that provided following gene delivery using 1764/pR15/MSVGFP/UL43.

REFERENCES

MacLean, A. R. et al., (1991), J. Gen. Virol. 72: 632–639.
Chou, J. et al., (1994), J. Virol. 68: 8304–8311.
Chou, J. and Roizmann B. (1992), PNAS 89: 3266–3270.
Gendler, S. J. et al.,(1990), J. Biol. Chem. 265:15286–15293.
Aicher, A. et al., (1997), Exp. Hematol. 25:39–44.
Samaniego, L. A. et al., (1995), J. Virol. 69:5705–5715.
Zitvogel, L. et al., (1996), J. Exp. Med 183:87–97.
Celluzzi, C. M. et al., (1996), J. Exp. Med. 183:283–287.
Reeves, M. E. et al., (1996), Cancer Research 56:5672–5677.
Arthur, J. F. et al., (1997), Cancer Gene Therapy 4:17–25.
Coffin, R. S. et al., (1998), Gene Therapy 5:718–722.
Coffin, R. S. and Latchnan, D. S. (1996), Genetic Manipulation of the Nervous System (D. S. Latchman Ed.) pp 99–114: Academic Press, London.
Inaba, K. et al., (1992) J. Exp. Med. 175:1157–1167.
Caux, C. et al., (1992), Nature 360:258–261.
Sallusto, F. and Lanzavecchia, A. (1994), J. Exp. Med. 179:1109–1118.
Coffin, R. S. et al., (1996), Gene Therapy 3:886–891.
Ace, C. I. et al., (1989), J. Virol. 63:2260–2269.
Smith, I. L. et al., (1992), Virology 186:74–86.
Rice, S. A. and Knipe, D. M. (1990), J. Virol. 64:1704–1715.
DeLuca, N. A. et al., (1985), J. Virol. 56: 558–570.
MacFarlane, M. et al., (1992), J. Gen. Virol. 73:285–292.
Lokensgard, J. R. et al., (1994), J. Virol. 68:7148–7158.
Maclean, C. A. et al., (1992), J. Gen. Virol. 72:897–906.
Gossen, M. and Bujard, H., (1992), PNAS 89:5547–5551.
Gossen, M. et al., (1995), Science 268:1766–1769.
Smiley, J. R. and Duncan, J. (1997), J. Virol. 71:6191–6193.
Gorman, C. M. (1985), DNA cloning, a practical approach. Glover, D. M. (Ed). IRAL Press: 143–190.
Soriano, P. C., Montgomery, R., Geske, and A. Bradley (1991), Cell 64:693–702.
Sekulovich, R. E., Leary, K. and Sandri-Goldin, R. M. (1988), J. Virol. 62:4510–4522.

What is claimed is:

1. An attenuated herpes simplex virus capable of efficiently infecting a dendritic cell without preventing antigen processing occurring within the infected cell, which virus lacks a functional UL43 gene and a functional vhs gene.

2. The virus of claim 1 which is a herpes simplex virus 1 or 2.

3. The virus of claim 1 which further lacks a functional ICP34.5 gene.

4. The virus of claim 1 which further lacks a functional VMW65 gene due to a mutation in said gene which abolishes its transcriptional-activation activity.

5. The virus of claim 1 which further lacks at least one functional immediate early gene.

6. The virus of claim 5 wherein said immediate early gene is selected from the group consisting of genes encoding ICP0, ICP4, ICP22 and ICP27.

7. The virus of claim 5 which lacks both a functional gene encoding ICP4 and a functional gene encoding ICP27 and which has an inactivating mutation in the gene encoding VMW65 abolishing its transcriptional activation activity.

8. The virus of claim 7 which lacks functional genes encoding ICP0, ICP4, ICP22 and ICP27.

9. The virus of claim 1 which further lacks a functional gene encoding ICP47.

10. The virus of claim 1 which comprises a heterologous gene.

11. The virus of claim 10 wherein said heterologous gene is operably linked to a control sequence permitting expression of said heterologous gene in a dendritic cell.

12. The virus of claim 10 wherein said heterologous gene encodes a polypeptide of therapeutic use.

13. The virus of claim 10 wherein said heterologous gene encodes a polypeptide, the level of expression of which is increased in or on the surface of tumour cells as compared to non-tumour cells; or a polypeptide which is present in or on the surface of tumour cells but absent from non-tumour cells; or a polypeptide capable of modifying immune responses.

14. The virus of claim 10 wherein said heterologous gene encodes a polypeptide of parasitic, viral or bacterial origin.

15. The virus of claim 10 wherein said heterologous gene encodes a tumour antigen.

16. The virus of claim 10 comprising more than one heterologous gene.

17. An isolated dendritic cell infected with a virus according to claim 1.

18. The isolated dendritic cell of claim 17 which is a human dendritic cell.

19. A process of producing a cell according to claim 18 comprising infecting, in vitro, a dendritic cell with an attenuated herpes simplex virus which virus lacks a functional UL43 gene and a functional vhs gene.

20. A pharmaceutical composition comprising a virus according to claim 1, or a cell containing said virus, together with a pharmaceutically acceptable carrier or diluent.

21. A method of stimulating an immune response in a human or animal subject, which method comprises administering to a subject in need thereof an effective amount of an attenuated herpes simplex virus capable of efficiently infecting a dendritic cell without preventing antigen processing occurring within the infected cell, which virus lacks a functional vhs gene and a functional UL43 gene.

22. The method of claim 21 wherein said virus is a herpes simplex virus 1 or 2.

23. The method of claim 21 wherein said virus further lacks a functional ICP34.5 gene.

24. The method of claim 21 wherein said virus further lacks a functional VMW65 gene due to a mutation in said gene which abolishes its transcriptional- activation activity.

25. The method of claim 21 wherein said virus further lacks at least one functional immediate early gene.

26. The method of claim 25 wherein said immediate early gene is selected from the group consisting of genes encoding ICP0, ICP4, ICP22 and ICP27.

27. The method of claim 25 wherein said virus lacks both a functional gene encoding ICP27 and a functional gene encoding ICP4 and which has an inactivating mutation in the gene encoding VMW65 abolishing its transcriptional activation activity.

28. The method of claim 25 wherein said virus lacks functional genes encoding ICP0, ICP4, ICP22 and ICP27.

29. The method of claim 21 wherein said virus lacks a functional gene encoding ICP47.

30. The method of claim 21 wherein said virus comprises a heterologous gene.

31. The method of claim 30 wherein said heterologous gene is operably linked to a control sequence permitting expression of said heterologous gene in a dendritic cell.

32. The method of claim 30 wherein said heterologous gene encodes a polypeptide of therapeutic use.

33. The method of claim 30 wherein said heterologous gene encodes a polypeptide, the level of expression of which is increased in or on the surface of tumour cells as compared to non-tumour cells; or a polypeptide which is present in or on the surface of tumour cells but absent from non-tumour cells; or a polypeptide capable of modifying immune responses.

34. The method of claim 30 wherein said heterologous gene encodes a polypeptide of parasitic, viral or bacterial origin.

35. The method of claim 30 wherein said heterologous gene encodes a tumour antigen.

36. The method of claim 30 wherein said virus comprises more than one heterologous gene.

37. The method of claim 21 wherein said virus is administered by infecting dendritic cells isolated or prepared from peripheral blood or bone marrow with said virus and administering said infected dendritic cells to said subject.

38. The method of claim 21, wherein the subject is in need of treatment of or protection against a pathogenic infection.

39. The method of claim 21, wherein the subject is in need of treatment of or protection against cancer.

* * * * *